US008211475B2

(12) United States Patent
Liang et al.

(10) Patent No.: US 8,211,475 B2
(45) Date of Patent: Jul. 3, 2012

(54) PROCESS FOR PREPARING NANOPARTICLES OF CHITOSAN IN WATER PHASE

(75) Inventors: Ke-Ming Liang, Hsinchu (TW);
Yen-Lin Chen, Hsinchu (TW);
Mei-Huei Chen, Hsinchu (TW);
Hing-Yuen Chan, Hsinchu (TW)

(73) Assignee: Food Industry Research and Development Institute, Hsinchu (TW)

( * ) Notice: Subject to any disclaimer, the term of this patent is extended or adjusted under 35 U.S.C. 154(b) by 638 days.

(21) Appl. No.: 12/266,464

(22) Filed: Nov. 6, 2008

(65) Prior Publication Data
US 2010/0021551 A1 Jan. 28, 2010

(30) Foreign Application Priority Data

Jul. 24, 2008 (TW) ............................... 97128151 A

(51) Int. Cl.
*A61K 9/50* (2006.01)
*A61K 47/00* (2006.01)
(52) U.S. Cl. ........................................ 424/499; 514/777
(58) Field of Classification Search .................. 424/499; 514/777
See application file for complete search history.

(56) References Cited

FOREIGN PATENT DOCUMENTS

| JP | 63161001 | 7/1988 |
| JP | 07-002701 | 1/1995 |
| JP | 07-053603 | 2/1995 |
| JP | 07-090245 | 4/1995 |
| JP | 09-031105 | 2/1997 |
| JP | 10072502 | 3/1998 |
| JP | 2003-026702 | 1/2003 |
| JP | 2005-287790 | 10/2005 |

OTHER PUBLICATIONS

Kiang, T.; Wen, J.; Lim, H. W.; Leong, K. W. The effect of the degree of chitosan deacetylation on the efficiency of gene transfection. Biomaterials 2004, 25, 5293-5301.*
Aiba, S. Preparation of N-acetylchitooligosaccharides by hydrolysis of chitosan with chitinase followed by N-acetylation. Carbohydrate Research 1994, 265, 323-328.*
da Trindade Neto, C. G.; Fernandes, A. L. P.; Santos, A. I. B.; Morais, W. A.; Navarro, M. V. M.; Dantas, T. N. C.; Pereira, M .R.; Fonseca, J. L. C. Preparation and characterization of chitosan-based dispersions. Polymer International 2005, 54, 659-666.*
Aiba, Carbohydrate Research, 1194, 265 (2), 323-328.*
da Trindade Neto et al. Polym. In. 2005, 54, 659-666.*
Kim et al. Bioconjugate Chem. 2001, 12, 932-938.*
Kiang et al. Biomaterials, 2004, 25, 5293-5301.*
Aiba, Carbohydrate Research, 1994, 265 (2), 323-328.*
English Translation of the previously submitted document (Chitin and Chitosan Handbook, Gihodo Shuppan Co., Feb. 25, 1995, pp. 232-236) in IDS filed on May 7, 2012.
TW office action issued on Apr. 10, 2012 for corresponding Taiwan application 097128151.
JP office action issued on Mar. 21, 2012 for corresponding Japan application 2008-288040.
Chitin and Chitosan Handbook, Gihodo Shuppan Co., Feb. 25, 1995, pp. 232-236.
Carbohydrate Research, 1976, vol. 47, pp. 315-320.

* cited by examiner

*Primary Examiner* — Fereydoun G Sajjadi
*Assistant Examiner* — Genevieve S Alley
(74) *Attorney, Agent, or Firm* — WPAT, P.C.; Anthony King

(57) ABSTRACT

A method for preparing chitosan nanoparticles in water phase is provided. The method comprises the following steps:
(a) providing a chitosan solution having a concentration of about 0.05 w/v % to about 1 w/v %,
(b) adding water first and then followed by acetic anhydride to the chitosan solution to carry out acetylation, wherein the concentration of acetic anhydride is from about 10 v/v % to about 30 v/v % of the total volume of the whole solution, and
(c) subjecting the solution from step (b) to physical dispersion.

14 Claims, No Drawings

PROCESS FOR PREPARING NANOPARTICLES OF CHITOSAN IN WATER PHASE

FIELD OF THE INVENTION

The present invention pertains to the production of chitosan nanoparticles. Especially, the present invention provides a method for preparing chitosan nanoparticles in water phase.

BACKGROUND OF THE INVENTION

Nowadays, in the field of pharmaceuticals, nanotechnology is widely applied in the research on medicine prophylaxis, diagnosis, drugs delivery and treatment of diseases. Nanoparticles are useful as carriers for drug delivery. They have many advantages, such as enhancing the stability of drugs in the gastrointestinal tract, improving the absorption and bioavailability of orally administered drugs, lowering the dosage of drugs so that the side effects caused by high dosage can be reduced, and administering drugs specifically. However, due to safety concerns, factors such as the source of materials and the reagents used tend to limit the applications of nanoparticles.

Chitosan is a drug carrier currently regarded as having extremely high safety ($LD_{50}$>4 g/kg). Generally, chitosan is processed and made into microspheres. For example, CN1698900 discloses a process for preparing chitosan drug carrying microspheres which is characterized by dissolving a hydrophilic medicament in an acetate-sodium acetate buffer solution to form an aqueous solution, pressing the aqueous phase into an oil phase through a microporous membrane with pressure to form milk-like droplets with a uniform dimension, and subjecting the droplets into a two-step hardening process so that they become a cross-linking solid form. The above-mentioned "two-step hardening process" comprises the step of adding an ionic gelatin agent (e.g., triphenyl phosphate (TPP)) to make the chitosan particles aggregate through their molecular chains, and that of adding a chemical cross-linking agent to make them become a cross-linking solid form. However, the method mentioned above cannot obtain the chitosan particles of nano scale.

Due to the formation of strong hydrogen bonds between chitosan and its adjacent molecules and organic acids (e.g., lactic acid), chitosan is hardly dissoluble in water. The solubility of chitosan in water becomes an important factor that influences chitosan's application. It is known that the water solubility of chitosan can be controlled by conducting an acetylation between chitosan and an acid anhydride under certain reaction conditions in organic phase to produce chitosan with different acetylation levels. Moreover, the preparation of chitosan nanoparticles is suggested.

US 2005/0226938 A1 discloses a method for preparing cross-linking core and core-shell nanoparticles polymers from chitosan which comprises reacting chitosan and at least one carboxylic acid having at least two carboxyl groups. Preferably, the activator used is carbodiimide.

US 2006/0013885 A1 discloses water-soluble chitosan nanoparticles for delivering an anticancer agent and a preparing method thereof. The method comprises linking chitosan molecules with methoxy poly(ethylene glycol) p-nitrophenyl carbonate to form amphipathic molecular chains, and then self-assembly to form chitosan nanoparticles.

JP 2006241321 discloses a method for producing chitosan nanoparticles which comprises dissolving chitosan in an aqueous acid solution to obtain an aqueous chitosan solution, and adding the aqueous chitosan solution to an aqueous alkali solution, for example, a 3N aqueous solution of sodium hydroxide.

CN 1686560 discloses a method for preparing tetra ammonium salt of chitin which comprises reacting chitosan with cyclopropyl-trimethyl-amine chloride to obtain a quaternary ammonium salt of chitosan, which is mixed with drugs to be encapsulated and sodium tripolyphosphate and then subjected to crosslink to obtain nanoparticles of quaternary ammonium salt of chitosan.

U.S. Pat. No. 4,996,307 discloses a process for preparing water-soluble acylated chitosan which comprises dissolving a water-soluble chitosan having a degree of deacetylation of at least 70% in an aqueous acid solution, diluting the solution with water or a water-miscible solvent such as methanol, and adding an acylation agent such as acetic anhydride to the diluted solution for acetylation. According to the examples of said US patent, an organic solvent, for example, methanol, ethanol or isopropanol, is used as an organic phase.

JP 2000256403 discloses a process for preparing partially acylated chitosan particles which comprises dissolving chitosan in an aqueous acid solution, dispersing the solution in a granulating solvent, agitating the dispersed phase to form particles. The process further comprises forming acylated chitosan particles through acetylation, adding an alkali to the particles and heating the same, partially deacetylating the particles, and then stabilizing them through a crosslinking reaction.

JP 62079201 discloses a process for producing porous granular N-acylated chitosan. In the process, a low-molecular weight chitosan is dissolved in an acidic aqueous solution, and the obtained solution is added to a basic solution to effect the aggregation of the chitosan solution and form the porous granular N-acylated chitosan. The acetylation is performed in an organic phase, for example, methanol or benzene.

CN 1367183 discloses a method for preparing hyaluronic acid-like chitosan which comprises making chitosan undergo an acylation reaction followed by a selective oxidation to obtain a chitosan derivative whose structure is similar to that of hyaluronic acid. The above-mentioned acylation is performed in an organic phase, for example, methanol.

Moreover, the publication entitled "N-Acetylchitosan Gel: A Polyhydrate of Chitin" (Shigehiro Hirano and Ryuji Yamaguchi, *BIOPOLYMER*, Vol. 15, 1685-1692 (1976)) compares the differences between the gelations resulting from the acetylations of an acetic acid solution of chitosan in methanol phase and in water phase. Said document essentially discusses the gelation resulting from the acetylation of chitosan, and the basic physical properties of gels obtained from said gelation. The physical properties discussed in said document include, for example, in which solvent the gel can be dissolved and the dissolvability of the gel. However, said document only teaches that the addition of a certain amount of acetic anhydride to water phase of chitosan leads to acetylation of chitosan and causes gel formation. The sizes of the resulting colloidal particles are usually too large. Even worse, the particles aggregate and result in a large mass. Chitosan nanoparticles cannot be produced under the operation conditions of said document.

Other relevant publications include: "Physicochemical properties and blood compatibility of acylated chitosan nanoparticles" (Dong-Won Lee et al., *Carbohydrate Polymers*, 58 (2004) 371-377) and "Reacetylated chitosan microspheres for controlled delivery of anti-microbial agents to the gastric mucosa" (A. Portero et al., MICROCAPSULATION, 19 (2002)), whose contents are incorporated herein for reference.

The known methods for preparing chitosan particles mentioned in the above all have one or more of the following disadvantages. First of all, no chitosan nanoparticles can actually be prepared. Second, the methods involve complicated chemical modification and are time- and labor-consuming. Third, the organic solvents utilized during the manufacture tend to remain in the resulting chitosan particles. Under such circumstances, even if chitosan nanoparticles are produced, whether they are safe for use in medical applications is worrisome.

There is still a need for a method for preparing chitosan nanoparticles which have good biocompatibility and are safe for medical applications.

SUMMARY OF THE INVENTION

The present invention provides a process for preparing chitosan nanoparticles in water phase which satisfies the need mentioned above. The process of the present invention comprises the steps of: providing a chitosan solution having a concentration of about 0.05 w/v % to about 1 w/v %, adding water first and then followed by acetic anhydride to the chitosan solution to carry out acetylation, wherein the concentration of acetic anhydride is about 10 v/v % to about 30 v/v % of the total volume of the whole solution, and subjecting the resulting solution to physical dispersion.

DETAILED DESCRIPTION OF THE INVENTION

The present invention provides a process for preparing chitosan nanoparticles in water phase, which comprises the following steps:
(a) providing a chitosan solution having a concentration of about 0.05 w/v % to about 1 w/v %;
(b) adding water first and then followed by acetic anhydride to the chitosan solution to carryout acetylation, wherein the concentration of acetic anhydride is about 10 v/v % to about 30 v/v % of the total volume of the whole solution; and
(c) subjecting the solution resulting from step (b) to physical dispersion.

In the process of the present invention, the chemical modification of the chitosan solution is chemically modified in water phase so as to convert the molecular chain of chitosan and make it amphipathic. Due to physical dispersion, the amphipathic molecular chain of chitosan undergoes self-assembly, which results in chitosan nanoparticles. During the formation of a gel from the modification of chitosan through acetylation, by controlling the concentrations of chitosan and acetic anhydride and utilizing physical dispersion, the present invention obtains chitosan particles of nano scale and avoids the formation of large gel mass as encountered in Shigehiro Hirano and Ryuji Yamaguchi's 1976 article.

Chitosan used in step (a) refers to β-[1→4]-2-amino-2-deoxy-D-glucopyranose, which has a wide variety of molecular weight, for example, 10 to 1,000 kDa, and usually has a degree of deacetylation ranging between 70% and 90%. Chitosan can be obtained from any known sources, which include but are not limited to mollusks (e.g., squids), shells of insects, algaes, crustaceans, and fungi. For chitosan obtained from crustaceans, shrimp shells and crab shells are preferred sources. For chitosan obtained from fungi, *Actinomucor taiwanensis* is the preferred source. The chitosan solution according to the present invention means a solution formed by dissolving chitosan in a solvent. The solvent can be any one that is known to dissolve chitosan, which includes but is not limited to an aqueous solution of acetic acid, formic acid, propanoic acid, malic acid, succinic acid, and lactic acid. An aqueous solution of acetic acid at a concentration of about 1 v/v % is preferred. The concentration of chitosan in the chitosan solution is preferably about 0.05 w/v % to about 0.6 w/v %, and more preferably about 0.1 w/v % to about 0.3 w/v %.

Acetic anhydride used in step (b) is commercially available. The concentration of acetic anhydride is about 10 v/v % to about 30 v/v %, preferably about 12.5 v/v % to about 25 v/v %, and more preferably about 17.5 v/v % to about 25 v/v %, of the total volume of the solution.

In the present invention, acetylation refers to the reaction between the amino group of chitosan and the carboxyl group of acetic anhydride, which results in an acetyl group. It can be conducted at any appropriate temperature known in the art.

The physical dispersion in step (c) refers to the treatment which is conducted in a physical manner to disperse the molecules within the solution. It can be conducted in any manner known in the art, which includes but is not limited to the utilization of a shaker or a spray sparger, or by means of mechanically stirring or ultrasonication. When the physical dispersion is conducted through stiffing, a magnetic stir bar can be added to the solution resulting from step (b) and the solution can be stiffed at an appropriate speed for a time period of over 24 hours. The stiffing speed depends on the volume of the reaction solution and can be, for example, about 150 rpm to about 1,500 rpm, preferably about 175 rpm to about 1,300 rpm. When the physical dispersion is conducted through ultrasonication, according to a preferred embodiment of the present invention, an ultrasonicator (Sonic & Materials Inc. Mode: VC 134, Power: 130 W, Vol.: 115 V, 50/60 Hz) can be used. The sonication time is about 5 minutes and the pulse interval is about 4 seconds, and the solution is immediately put in an ice bath after the completion of sonication.

The physical dispersion of step (c) can be conducted at any appropriate temperature known in the art, for example, about 20° C. to about 40° C. When the physical dispersion is conducted by mechanical stirring, it is preferably performed at about 37° C. When the physical dispersion is conducted by ultrasonication, it is preferably performed at room temperature.

The chitosan nanoparticles obtained from the process of the present invention have an average diameter of about 100 nm to about 500 nm, preferably about 100 nm to about 300 nm, and more preferably 100 nm to about 200 nm.

The process of the present invention can obtain chitosan nanoparticles under mild conditions without using an organic solvent or the complicated steps for chemical modification. Because the whole procedure of the process of the present invention is carried out in water phase, the conventional chitosan nanoparticles' problematic tendency to contain organic solvent residue can be avoided. Therefore, the chitosan nanoparticles obtained from the process of the present invention not only are safe for pharmacological applications but also have better bioavailability.

The invention will become apparent with reference to the following examples, which are purely for illustration and should not be taken to limit the scope of the invention as described in the claims. Any obvious modification and change which can be easily accomplished by persons having ordinary skill in the technical field to which the present invention belongs are within the disclosure of the specification and the attached claims of the present case.

EXAMPLE

Example 1

Preparation of Chitosan Nanoparticles (Using a Magnetic Stir)

(I) Starting with Chitosan Samples Obtained from Different Sources and Having Different Molecular Weights The chitosan samples with different average molecular weights obtained from shrimp/crab shells were purchased from Shin Era Technology Co., Ltd., Taiwan, ROC, and the chitosan samples with different average molecular weights were obtained from fungus (*Actinomucor taiwanensis*, purchased from the Food Industry Research and Development Institute, Taiwan, ROC). 0.2 g each of the chitosan samples was dissolved in a pre-formulated 1 v/v % acetic acid aqueous solution. The volumes of the chitosan solutions were then adjusted to 100 ml with water. 10 ml each of the above-mentioned chitosan solutions were taken out for subsequent reactions. In order to carry out acetylation, 5 ml of Milli Q pure water were first added to each of the 10 ml chitosan solutions and then followed by 5 ml of 100% acetic anhydride (i.e., the volume ratio of pure water to acetic anhydride was 1:1). In this reaction, the total volume of each reaction solutions was 20 ml, and the concentration of acetic anhydride was 25 v/v % of the total volume of the reaction solution. A magnetic stir bar was added to each of the solutions. The solutions were stirred at 37° C. with a speed of 1,300 rpm for over 24 hours. The chitosan nanoparticles formed within the solutions were analyzed by using a nanoparticle sizing analyzer, and the results were given in Table 1. As shown in Table 1, the average particle sizes of the obtained chitosan nanoparticles range from 195 to 326 nm.

TABLE 1

| Chitosan source | Average molecular weight (kDa) | average particle size (nm) |
| --- | --- | --- |
| CC 68 | 68 | 233 |
| CC 72 | 72 | 243 |
| CC 95 | 95 | 247 |
| FC 24 | 24 | 195 |
| FC 190 | 190 | 299 |
| FC 340 | 340 | 326 |

Note:
CC represents the chitosan obtained from shrimp/crab shells.
FC represents the chitosan obtained from fungus.
The numbers represent the average molecular weight (kDa) of the chitosan.

(II) Using Different Concentrations of Chitosan and Acetic Anhydride

The experiment conditions of Central Composite Design (CCD) experiment were determined by Design-Expert 6.0.2 software. A flask test was conducted under the experiment conditions determined by the software. The test results were entered in the experimental table designed by the software. Through the analysis of the software, concrete conclusions associated with variable factors were obtained. The CCD design experiment utilized in the examples of the present case makes it possible to discuss multiple variable factors in one experiment. Unlike the present invention, traditional experimental design can only discuss one variable factor at a time. According to the variable factors determined by Design-Expert 6.0.2, including the reaction conditions and the trial numbers, one can conduct a flask test using the designed experimental conditions. After entering the results of the flask test and statistically analyzing the results by the software, one can understand how each single variable factor influences the results of the experiment, and how every two variable factors reciprocally affect the results of the experiment.

(1) In this example, the chitosan sample (CC 95) obtained from shrimp/crab shells with a molecular weight of 95 kDa (commercially available from Shin Era Technology Co., Ltd., Taiwan, ROC) was used to conduct the above-mentioned CCD design experiment.

0.05, 0.20 and 0.35 g of the chitosan sample mentioned above were individually dissolved in a pre-formulated 1 v/v % acetic acid aqueous solution. The volumes of the chitosan solutions were then adjusted to 100 ml with water. 5 ml each of the above-mentioned chitosan solution were taken out for subsequent reactions. In order to carry out acetylation, 2.5 ml of Milli Q pure water were first added to each of the 5-ml chitosan solutions and then followed by 2.5 ml of 100% acetic anhydride (i.e., the volume ratio of pure water to acetic anhydride was 1:1). In this reaction, the total volume of each reaction solution was 10 ml, and the concentration of acetic anhydride in each solution 25 v/v % was of the total volume of the reaction solution. Acetylation was carried out under the same conditions as those described in (1). The results showed that of chitosan nanoparticles could be obtained from all of the aqueous solutions prepared with different concentrations of chitosan. The chitosan nanoparticles formed within the aqueous solutions were analyzed by using a nanoparticle sizing analyzer, and the results were given in Table 2. As shown in Table 2, the average particle sizes of the obtained chitosan nanoparticles range from 189 to 298 nm.

TABLE 2

| Test | Concentration of acetic anhydride (v/v %) | Concentration of chitosan (w/v %) | Average particle size (nm) |
| --- | --- | --- | --- |
| 1 | 25 | 0.05 | 189 |
| 2 |  | 0.20 | 245 |
| 3 |  | 0.35 | 298 |

(2) In this example, the chitosan sample (FC 24) obtained from fungus *Actinomucor taiwanensis* (commercially available from Food Industry Research And Development Institute, Taiwan, ROC) with a molecular weight of 24 kDa was used to conduct the above-mentioned CCD design experiment 0.4 g and 0.6 g of the chitosan sample were individually dissolved in a pre-formulated 1 v/v % acetic acid aqueous solution. The volumes of the chitosan solutions were then adjusted to 100 ml with water. 5 ml each of the above-mentioned chitosan solutions were taken out for subsequent reactions. In order to carry out acetylation, 2.5 ml of Milli Q pure water were first added to each of the 5-ml chitosan solutions and then followed by 2.5 ml of 100% acetic anhydride (i.e., the volume ratio of pure water to acetic anhydride was 1:1). In this reaction, the total volume of each reaction solution was 10 ml, and the concentration of acetic anhydride was 25 v/v % of the total volume of the reaction solution. A magnetic stir bar was added to each of the solutions. The solutions were stirred at 37° C. at a speed of 175 rpm for over 24 hours. The chitosan nanoparticles formed within the aqueous solutions were analyzed by using a nanoparticle sizing analyzer, and the results were given in Table 3. As shown in Table 3, the average particle sizes of the obtained chitosan nanoparticles range from 196 to 206 nm.

TABLE 3

| Test | Concentration of acetic anhydride (v/v %) | Concentration of chitosan (w/v %) | Average particle size (nm) |
|---|---|---|---|
| 1 | 25 | 0.4 | 197 |
| 2 |  | 0.4 | 206 |
| 3 |  | 0.6 | 196 |
| 4 |  | 0.6 | 196 |

As shown by the results in Tables 2 and 3, the process of the present invention can obtain chitosan nanoparticles from chitosan of a concentration ranging from 0.1 w/v % to 0.6 w/v %.

(3) Following the above-mentioned experiments, 0.2 g of chitosan CC 95 was dissolved in a pre-formulated 1 v/v % acetic acid aqueous solution. The volume of the chitosan solution was then adjusted to 100 ml with water. 5 ml of the above-mentioned chitosan solution was taken out for subsequent reactions. In order to carry out acetylation, different volumes of Milli Q pure water were first added to the 5-ml chitosan solution and followed by different volumes of acetic anhydride. In this reaction, the total volume of each reaction solution was 10 ml, and the concentrations of acetic anhydride were 17.5 v/v % and 25 v/v % of the total volume of the reaction solutions. Acetylation was carried out under the same conditions as described in (2). The chitosan nanoparticles formed within the solutions were analyzed by using a nanoparticle sizing analyzer, and the results were given in Table 4. As shown in Table 4, the average particle sizes of the obtained chitosan nanoparticles range from 170 to 245 nm. In conclusion, the process of the present invention can obtain chitosan nanoparticles at acetic anhydride concentrations of 17.5 v/v % to 25 v/v %.

TABLE 4

| Test | Concentration of chitosan (w/v %) | Concentration of acetic anhydride (v/v %) | Average particle size (nm) |
|---|---|---|---|
| 1 | 0.2 | 17.5 | 170 |
| 2 |  | 25 | 245 |

Example 2

Preparation of Chitosan Nanoparticles (Using an Ultrasonicator)

(I) Starting with Chitosan Samples Obtained from Different Sources and Having Different Molecular Weights The chitosan samples with different average molecular weights obtained from shrimp/crab shells were purchased from Shin Era Technology Co., Ltd., Taiwan, ROC, and the chitosan samples with different average molecular weights were obtained from fungus (*Actinomucor taiwanensis*, purchased from the Food Industry Research and Development Institute, Taiwan, ROC). 0.2 g each of the chitosan samples was dissolved in a pre-formulated 1 v/v % acetic acid aqueous solution. The volumes of the chitosan solutions were then adjusted to 100 ml with water. 3.6 ml each of the above-mentioned chitosan solutions were taken out for subsequent reactions. In order to carry out acetylation, different volumes of Milli Q pure water were first added to each of the 3.6-ml chitosan solutions and then followed by different volumes of 100% acetic anhydride (i.e., the volume ratios of pure water to acetic anhydride were 1:2, 2:3 and 1:1). In this reaction, the total volume of each reaction solution was 7.2 ml, and the concentrations of acetic anhydride were 16.67 v/v %, 20 v/v % and 25 v/v % of the total volumes of the reaction solutions. The physical dispersion was conducted at room temperature with an ultrasonicator (Sonic & Materials Inc. Mode: VC 134) with an output work of 15 W for 5 minutes at a 4-second pulse interval (the sonicator was placed in the reaction device (i.e., a tube)). The solution was moved to an ice bath soon after the completion of sonication, and thereby an aqueous solution of chitosan nanoparticles was obtained. The chitosan nanoparticles formed within the solutions were analyzed by using a nanoparticle sizing analyzer, and the results were given in Table 5. As shown in Table 5, the average particle sizes of the obtained chitosan nanoparticles range from 138 to 213 nm.

TABLE 5

| Concentration of acetic anhydride (v/v %) | Sample | Average particle size (nm) |
|---|---|---|
| 16.67 | CC 68 | 148 |
|  | FC 90 | 138 |
|  | FC 340 | 180 |
| 20 | CC 68 | 198 |
|  | CC 72 | 158 |
|  | CC 75 | 140 |
|  | FC 90 | 150 |
|  | FC 340 | 170 |
| 25 | FC 24 | 213 |
|  | FC 30 | 170 |

Note:
In the "Sample" column of Table 5,
CC represents the chitosan obtained from shrimp/crab shells.
FC represents the chitosan obtained from fungus.
The numbers portion represent the average molecular weight (kDa) of the chitosan.

The results in Table 5 show that according the process of the present invention, chitosan nanoparticles having an average particle size ranging from 138 to 213 nm can be obtained by using chitosan samples obtained from different sources (e.g., from shrimp/crab shells and fungus) and having different average molecular weights at a concentration of acetic anhydride ranging from 16.67 to 25 v/v % with the utilization of an ultrasonicator.

(II) Using Different Final Concentrations of Acetic Anhydride

In this example, the chitosan samples (FC 340) obtained from fungus *Actinomucor taiwanensis* (commercially available from the Food Industry Research And Development Institute, Taiwan, ROC) with a molecular weight of 340 kDa were used.

0.2 g of chitosan FC 340 was dissolved in a pre-formulated 1 v/v % acetic acid aqueous solution. The volume of the chitosan solution was then adjusted to 100 ml with water. 2 ml of the above-mentioned chitosan solution were taken out for subsequent reactions. In order to carry out acetylation, different volumes of Milli Q pure water were first added to the 2 ml chitosan solution and followed by different volumes of acetic anhydride (i.e., the volume ratios of pure water to acetic anhydride were 1:1, 3:5 and 1:3). In this reaction, the total volume of each reaction solutions were 4 ml, and the concentrations of acetic anhydride were 25 v/v %, 18.75 v/v % and 12.5 v/v % of the total volumes of the reaction solution. The physical dispersion was conducted with the ultrasonicator and conditions identical to those mentioned in (I). An aqueous solution of chitosan nanoparticles was obtained. The chitosan nanoparticles formed within the solutions were analyzed by using a nanoparticle sizing analyzer, and the results were given in Table 6. As shown in Table 6, the average particle sizes of the obtained chitosan nanoparticles range from 153 to 170 nm.

TABLE 6

| Concentration of acetic anhydride (v/v %) | Average particle size (nm) |
|---|---|
| 25 | 170 |
| 18.75 | 165 |
| 12.5 | 153 |

The results of Table 6 show that according the process of the present invention, chitosan nanoparticles having an average particle size ranging from 153 to 170 nm can be obtained by using the fungal chitosan sample FC 340 at the concentrations of acetic anhydride of 16.67 to 25 v/v %, 12.5 v/v %, 18.75 v/v % and 25 v/v % with the utilization of an ultrasonicator.

In view of the results of Examples 1 and 2, it is known that chitosan nanoparticles can be obtained by using the chitosan samples obtained from different sources (e.g., from shrimp/crab shells and fungus) and having different average molecular weights at a concentration of acetic anhydride ranging from 12.5 v/v % to 25 v/v % with the utilization of physical dispersion (e.g., by stirring or ultrasonication).

What is claimed is:

1. A method for preparing chitosan nanoparticles in an aqueous solution consisting of the following steps: (a) providing a chitosan solution having a concentration of about 0.05 w/v % to about 1 w/v %, wherein the chitosan solution is formed by dissolving chitosan in a solvent, and the solvent is an aqueous solution selected from acetic acid, formic acid, propanoic acid, malic acid, succinic acid and lactic acid; (b) adding water followed by acetic anhydride to the chitosan solution to carry out acetylation, wherein the concentration of acetic anhydride is about 10 v/v % to about 30 v/v % of the total volume of the whole solution; and (c) subjecting the solution from step (b) to physical dispersion.

2. The method according to claim 1, wherein the chitosan is obtained from crustaceans or fungi.

3. The method according to claim 1, wherein the solvent is an aqueous solution of acetic acid at a concentration of about 1 v/v %.

4. The method according to claim 1, wherein the concentration of chitosan in the chitosan solution ranges from about 0.05 w/v % to about 0.6 w/v %.

5. The method according to claim 4, wherein the concentration of chitosan in the chitosan solution ranges from about 0.1 w/v % to about 0.3 w/v %.

6. The method according to claim 1, wherein the concentration of acetic anhydride ranges from about 12.5 v/v % to about 25 v/v % of the total volume of the whole solution.

7. The method according to claim 6, wherein the concentration of acetic anhydride ranges from about 17.5 v/v % to about 25 v/v % of the total volume of the whole solution.

8. The method according to claim 1, wherein the physical dispersion in step (c) is conducted by mechanically stifling or ultrasonication.

9. The method according to claim 8, wherein the mechanically stirring is carried out by adding a magnetic stir bar to the solution from step (b) and stifling the solution at a speed of about 150 rpm to about 1,500 rpm.

10. The method according to claim 8, wherein the ultrasonication is carried out at a power of about 15 W.

11. The method according to claim 1, wherein the physical dispersion is carried out at about 20° C. to about 40° C.

12. The method according to claim 1, wherein the chitosan nanoparticles prepared have an average particle size of about 100 nm to about 500 nm.

13. The method according to claim 12, wherein the chitosan nanoparticles have an average particle size of about 100 nm to about 300 nm.

14. The method according to claim 13, wherein the chitosan nanoparticles have an average particle size of about 100 nm to about 200 nm.

* * * * *